(12) United States Patent
Fenton et al.

(10) Patent No.: US 8,021,370 B2
(45) Date of Patent: Sep. 20, 2011

(54) INSTRUMENT FOR POSITIONING A CUP COMPONENT OF AN ORTHOPAEDIC JOINT PROSTHESIS

(75) Inventors: Gary Fenton, Huddersfield (GB); Stefano Alfonsi, Fort Wayne, IN (US); Gary Moore, Wetherby (GB); Magnus Flett, Wakefield (GB)

(73) Assignee: Depuy International Ltd. (GB)

( * ) Notice: Subject to any disclaimer, the term of this patent is extended or adjusted under 35 U.S.C. 154(b) by 799 days.

(21) Appl. No.: 10/587,733

(22) PCT Filed: Feb. 3, 2004

(86) PCT No.: PCT/GB2004/000405
§ 371 (c)(1),
(2), (4) Date: Dec. 1, 2006

(87) PCT Pub. No.: WO2004/069107
PCT Pub. Date: Aug. 19, 2004

(65) Prior Publication Data
US 2007/0250066 A1 Oct. 25, 2007

(30) Foreign Application Priority Data
Feb. 3, 2003 (GB) .................................. 0302409.8

(51) Int. Cl.
*A61B 17/60* (2006.01)
*A61B 17/58* (2006.01)
*A61F 2/00* (2006.01)
(52) U.S. Cl. ............................................. 606/91; 606/99
(58) Field of Classification Search .............. 606/9, 991, 606/1, 91–99, 79–81
See application file for complete search history.

(56) References Cited

U.S. PATENT DOCUMENTS

| | | | |
|---|---|---|---|
| 4,023,572 A * | 5/1977 | Weigand et al. ................. | 606/81 |
| 4,408,360 A | 10/1983 | Keller et al. | |
| 4,632,111 A | 12/1986 | Roche | |
| 5,169,399 A * | 12/1992 | Ryland et al. .................... | 606/91 |
| 5,171,243 A | 12/1992 | Kashuba et al. | |
| 5,171,313 A * | 12/1992 | Salyer .......................... | 606/86 R |
| 5,236,433 A * | 8/1993 | Salyer .............................. | 606/91 |
| 5,364,403 A * | 11/1994 | Petersen et al. ................. | 606/91 |
| 5,486,181 A * | 1/1996 | Cohen et al. ..................... | 606/91 |
| 5,540,697 A * | 7/1996 | Rehmann et al. ............... | 606/91 |

(Continued)

FOREIGN PATENT DOCUMENTS
FR 2583634 12/1986
(Continued)

OTHER PUBLICATIONS
GB Search Report dated Jul. 21, 2003.
(Continued)

*Primary Examiner* — Thomas C Barrett
*Assistant Examiner* — Matthew Lawson

(57) ABSTRACT

An instrument for positioning a cup component of an orthopaedic joint prosthesis includes a shaft, and a flange located near an end of the shaft on which the cup component can be fixed. The flange extends from the shaft transversely, and can be retracted from an in-use position wherein the flange is received in a groove in the internal surface of the cup component when positioned over the said end of the instrument, and a retracted position in which the flange is withdrawn toward the axis of the shaft from the in-use position, allowing the cup component to be released from the instrument.

18 Claims, 2 Drawing Sheets

U.S. PATENT DOCUMENTS

| | | | | |
|---|---|---|---|---|
| 5,571,111 | A | * | 11/1996 | Aboczky ........................ 606/91 |
| 5,571,200 | A | * | 11/1996 | Cohen et al. ............... 623/22.12 |
| 5,584,837 | A | * | 12/1996 | Petersen ........................ 606/91 |
| 5,928,287 | A | * | 7/1999 | Keller ....................... 623/22.21 |
| 5,954,727 | A | | 9/1999 | Collazo |
| 6,013,082 | A | * | 1/2000 | Hiernard et al. ............... 606/99 |
| 6,063,124 | A | | 5/2000 | Amstutz et al. |
| 6,132,469 | A | * | 10/2000 | Schroeder ................. 623/22.24 |
| 2005/0131420 | A1 | * | 6/2005 | Techiera et al. ................ 606/99 |
| 2006/0229630 | A1 | * | 10/2006 | Collins et al. .................. 606/91 |

FOREIGN PATENT DOCUMENTS

| | | |
|---|---|---|
| GB | 2299758 | 10/1998 |
| WO | WO 9421199 A1 | 9/1994 |

OTHER PUBLICATIONS

International Search Report dated May 12, 2004.

PCT Written Opinion.

* cited by examiner

INSTRUMENT FOR POSITIONING A CUP COMPONENT OF AN ORTHOPAEDIC JOINT PROSTHESIS

This invention relates to an instrument for positioning a cup component of an orthopaedic joint prosthesis.

Certain orthopaedic joint prostheses include a hollow cup with an inner surface which defines a generally hemispherical hollow region, and another component which has a spherical part which can be received in the hollow region for articulation relative to the cup component. Such joint prostheses can include hip joint prostheses and shoulder joint prostheses. The exterior of the cup will contact the prepared surface of the patient's bone in which the component is to be implanted. The interior of the cup will present a smooth bearing surface to the spherical part of the other component of the joint prosthesis. The bearing surface can be provided by a single piece cup component. Alternatively, the cup component can comprise a bearing part which provides the bearing surface, and which fits into a shell part. The bearing part can be made from a material which is different from the material of the shell part: for example the bearing part can be made from a polymeric material (such as polyethylene) and the shell part (and the spherical part of the other component) can be made from a metal (such as a cobalt-chromium based alloy, or a stainless steel, or a titanium based alloy).

It is important that the components of an orthopaedic joint prosthesis are positioned accurately in a patient's bone. Both location and alignment are important. Accurate positioning of a component requires that the component be engaged by an appropriate instrument, allowing considerable force to be applied to the component if and as necessary. However, it can be important not to contact the external surface or the internal surface or both of the component with the instrument, especially the internal surface when it has been provided with a smooth polished bearing surface. Scratching or otherwise damaging that surface can impair the bearing properties of the prosthesis.

U.S. Pat. No. 5,171,243 discloses an acetabular cup for use in a hip joint prosthesis. The cup comprises a shell which has a circumferential groove cut into its inner surface. The groove can received a flange at the free end of an insertion tool so that the cup is retained on the instrument, allowing the shell to be manipulated using the instrument. The grooved shell part receives a bearing part which has a smooth inner surface against which a bearing surface of another component of the joint prosthesis can articulate. The shell part can have fastening holes extending through its wall through which bone screws can extend to fasten the shell part to the surface of a bone.

The present invention provides an instrument which relies on a retractable flange to secure it to a cup component having a groove in its internal surface Accordingly, in one aspect, the invention provides an for positioning a cup component of an orthopaedic joint prosthesis, which comprises a shaft, and a flange towards the end of the shaft on which the cup component can be fixed, which extends from the shaft transversely, and which can be retracted from an in-use position in which the flange can be received in a groove in the internal surface of the cup component, when positioned over the said end of the instrument, and a retracted position in which the flange is withdrawn towards the axis of the shaft from the in-use position, allowing the cup component to be released from the instrument, in which the flange comprises at least two radially spaced apart flange portions (for example two, three or four flange portions), at least one of the flange portions being retractable as specified above and biassed towards the in-use position by means of a spring element which is made of a material which is different from that of the flange portion.

The use of different materials for the spring element and the flange portion allows the materials of the two components to be optimised for their respective functions. The flange portion can be made of a metal (such as stainless steel or another metal as commonly used in the manufacture of surgical instruments). The spring element might also be formed from a metal, but generally a different metal from that of the flange portion. Preferably, the spring element s formed from a non-metallic material, such as an elastomer. Suitable elastomeric materials include certain rubbers, especially silicone rubbers.

Preferably, the instrument includes a support which extends transversely, generally parallel to the flange, and in which the movement of the retractable flange portion between the retracted and in-use positions is in a direction which is parallel to the support.

Preferably, the support comprises at least one support plate which the retractable flange portion slides against. Preferably, the support presents a pair of opposite support surfaces and the retractable flange portion slides between them. It is particularly preferred that the support presents a support surface which the side of the retractable flange portion facing towards the end of the instrument can slide against. This can help to support the flange against forces which tend to separate the prosthesis component from the instrument.

In another aspect, the invention provides an instrument for positioning a cup component of an orthopaedic joint prosthesis, which comprises a shaft, and a flange towards the end of the shaft on which the cup component can be fixed, which extends from the shaft transversely, and which can be retracted from an in-use position in which the flange can be received in a groove in the internal surface of the cup component, when positioned over the said end of the instrument, and a retracted position in which the flange is withdrawn towards the axis of the shaft from the in-use position, allowing the cup component to be released from the instrument, in which the instrument includes a transverse support which extends generally parallel to the flange, and in which the flange comprises at least two radially spaced apart flange portions (for example two, three or four flange portions), at least one of the flange portions being retractable as specified above while being supported by the support, the movement of the retractable flange portion between the retracted and in-use positions being in a direction which is parallel to the support plate, the retractable flange portion being biassed towards the in-use position.

Preferably, the retractable flange portion is biassed towards the in-use position by means of a spring element which is made of a material which is different from that of the flange portion.

Preferably, the spring element is formed from a non-metallic material. The spring element can be positioned between the flange portion and the axis of the shaft. The spring element can be compressed elastically by the flange portion when the flange portion is moved from its in-use position towards its retracted position.

A preferred spring element comprises an O-ring which is positioned between the retractable flange portion and the shaft. Preferably, the flange is located so that it extends around the shaft. Preferably, the or each retractable flange portion has an upstand which, when the flange portion is moved from its in-use position towards its retracted position, contacts the O-ring and causes it to be compressed. The upstand will normally extend generally along (for example parallel to) the axis of the instrument, for example towards the end of the tool. However, the upstand can extend along the axis of the instrument in the direction away from the end of the tool.

Preferably, the instrument includes a pressuring plate which is fixed relative to the shaft with the flange between the plate and the said end of the shaft, for engaging the open mouth of the cup component to apply force to it, in which the edge of the plate is chamfered so that its transverse dimension is greatest at about the surface which contacts the cup component.

In a further aspect, the invention provides an instrument for positioning a cup component of an orthopaedic joint prosthesis, which comprises (a) a shaft, (b) a flange towards the end of the shaft on which the cup component can be fixed, which extends from the shaft transversely, and which can be retracted from an in-use position in which the flange can be received in a groove in the internal surface of the cup component, when positioned over the said end of the instrument, and a retracted position in which the flange is withdrawn towards the axis of the shaft from the position in which it can be received in a groove in the cup component, allowing the cup component to be released from the instrument, and (c) a pressuring plate which is fixed relative to the shaft with the flange between the plate and the said end of the shaft, for engaging the open mouth of the cup component to apply force to it.

Preferably, the edge of the plate is chamfered so that its transverse dimension is greatest at about the surface which contacts the cup component.

Preferably, the transverse dimension of the pressurising plate is greater than that of flange when the flange is in its in-use position. This can help to ensure that the pressurising plate properly contacts the cup around its open mouth, so that force is applied accurately to the cup.

Preferably, the face of the flange which faces towards the said end of the shaft is chamfered at its edge. This can facilitate inward displacement of the flange so that it can be received in the groove, when the instrument is offered to the open mouth of the cup component.

Preferably, the instrument includes at least three radially spaced apart flange portions.

Preferably, the instrument includes a soft cap which is positioned between the flange and the said end of the shaft, and which at least partially surrounds the end of the shaft. The cap preferably extends around the shaft, for example generally in the form of a skirt. Preferably it also covers the end of the shaft (although the end can be left exposed). The material of the cap will be selected so that it will not damage the smooth polished internal surface of the cup component. Suitable materials include polymeric materials and elastomeric materials, such as polyethylene, silicone rubber etc.

In a yet further aspect, the invention provides a cup component of an orthopaedic joint prosthesis, which has an external surface, a generally circular open mouth and an internal surface defining a generally hemispherical hollow region with a smooth bearing surface, in which a generally spherical part of another component of the joint prosthesis can be received for articulation relative to the cup component, in which the internal surface has a groove formed in it around at least part of the periphery of the component, the groove being defined by an inner lip, and an opposite outer lip which is closer to the open mouth, in which (a) the angle that is subtended at the centre of the hollow region between the edge of the cup component at the open mouth and the inner lip of the groove is not more than about 10°, and (b) the outer lip is displaced radially outwardly relative to the inner lip.

The component of the invention has the advantage that it can be engaged by an instrument having a flange which can fit into the groove, and that the cup can present sufficient area of the internal surface for this surface to provide for articulation with the bearing surface of another component. Accordingly, when the component is a metal shell which is intended to be used without a bearing part within it (as can be the case in a joint prosthesis in which both bearing surfaces are provided by metals, or one is provided by a metal and other is provided by ceramic (including metal with a ceramic coating), the groove allows the component to be manipulated prior to fixation to the patient's bone tissue. However, the cup component of the invention can be a bearing part which has to be manipulated relative to a shell after the shell has been located and fixed relative to the patient's bone tissue.

Surprisingly, it has been found that it is possible to achieve secure fixation of the cup component of the invention to an instrument using a flange which is received in the groove, when the groove is positioned close to the open mouth of the cup. Furthermore, it has been found that the material of the cup close to the mouth, in which the groove is formed and which provides the outer lip, can provide little or no restriction on the range of articulation of a joint of which the cup component forms a part. This is facilitated by the outer lip being displaced radially outwardly relative to the inner lip. The nature of this radial displacement can be understood in terms of comparing the actual location of the outer lip relative to a line which represents the continuation of the internal surface of the component through the region in which the groove is located. When the hollow space defined by the interior surface is spherical (as will often be the case), the displacement is determined by comparing the radius of the cup at the inner and outer lips. The extent of the displacement will depend on (a) providing the groove with sufficient depth that it can be engaged securely by a flange on an instrument, and (b) minimising the likelihood of the cup component being contacted by the other component of the joint during articulation, other than on the internal bearing surface. Preferably, the ratio of the radius of the cup component at the inner lip of the groove to the radius of the cup component at the outer lip of the groove is not more than about 0.99, more preferably not more than about 0.98, especially not more than about 0.97, for example not more than about 0.95. Preferably, the said ratio is at least about 0.85, more preferably at least about 0.90, for example at least about 0.95. The difference between the radii is preferably at least about 0.5 mm, more preferably at least about 1.0 mm. The difference between the radii is preferably not more than about 2.5 mm, more preferably not more than about 2.0 mm.

Preferably, the internal surface is chamfered at the open mouth, around at least part of the periphery of the component, more preferably around substantially all of the periphery. The provision of a chamfer on the internal surface can help to reduce further the likelihood of the cup component being contacted by the other component of the joint during articulation, other than on the internal bearing surface. Preferably, the angle of the chamfer, between the chamfered internal surface and a tangent to the internal surface at the point at which the chamfered surface intersects the generally spherical surface, is at least about 20°, more preferably at least about 30°, for example at least about 40° or 45°.

Preferably, the chamfer on the internal surface extends through at least about 20% of the thickness of the component, more preferably at least about 25%, especially at least about 30%.

Preferably, the external surface is chamfered at the open mouth, around at least part of the periphery of the component, more preferably around substantially all of the periphery. This can minimise obstruction to view of bone tissue immediately surrounding the site at which the component is implanted, and greatly facilitate accurate location of the component, in particular to ensure that the component can be seen to have been seated properly in the prepared recess in the bone before it is fixed in position.

Preferably, the angle between the chamfered external surface and a tangent to the non-chamfered part of the external surface is at least about 30°. Preferably, the chamfer on the external surface extends through at least about 20% of the thickness of the component, more preferably at least about 25%, especially at least about 30%.

Preferably, the cup component has a planar face at the mouth substantially perpendicular to the polar axis of the component, extending around at least part of the mouth of the component, and preferably extending around all of the component. When each of the internal and external surfaces of the component is chamfered, the planar face is provided between those chamfered faces. The provision of a planar face allows the component to be engaged by a plate to apply force to the component in a direction generally along the polar axis, to push the component into the prepared recess in the patient's bone.

The cup component of the invention will often be rotationally symmetrical around the polar axis, although there can be deviations from such symmetry. For example, the mouth of the component might not necessarily fall in a single plane. perpendicular to the polar axis. For example, the component might include an extension of the internal surface around only part of its perimeter to reduce the risk of dislocation of the joint. The hollow region within the cup component will generally have a spherical shape, although there can be deviations from sphericity. For example, the radius of the sphere can be slightly greater at or towards the equator compared with that at the pole. Frequently, when there are such deviations, they will be such that the internal surface is rotationally symmetrical. It will also generally be preferred for the deviations to be small.

Preferably, the angle that is subtended at the centre of the hollow region between the inner lips of the groove at two diametrically opposite points is at least about 150°, more preferably at least about 155°, especially at least about 160°. The angle will generally be less than 180°. The material which defines the groove falls outside this subtended angle.

The angle that is subtended at the centre of the hollow region between the edge of the cup component at the open mouth and the inner lip of the groove is not more than about 10°, preferably not more than about 7°, for example about 5°. Designing the component with this angle as small as possible can help to minimise the likelihood of the cup component being contacted by the other component of the joint during articulation, other than on the internal bearing surface.

The walls of the groove can be generally parallel, at least at the open end of the groove. This can ensure that a parallel walled flange is a sliding fit in the groove allowing the flange to be introduced easily into the groove and to be withdrawn from the groove, and that the play between the component and the instrument (which provides the flange) is small.

The width of the groove (measured between its opposite walls) at the open end will depend on factors such as the size of the component and the amount of force that has to be applied to the component as it is manipulated during implantation. The width of the groove will generally be not more than about 3.0 mm, preferably not more than about 2.5 mm, more preferably not more than about 2.0 mm, especially not more than about 1.5 mm, for example not more than about 1.0 mm.

The cup component can be made from a metal, especially when its external surface is intended to contact the patient's bone tissue. Suitable metals include cobalt-chromium based alloys, or certain stainless steels, or titanium or a titanium based alloy. The external surface can be fixed in the prepared cavity in the bone tissue using bone cement. Alter-natively, the external surface can be configured for cementless fixation, for example by provision of a porous surface, such as is available from DePuy Orthopaedics Inc under the trade mark POROCOAT. The cup component can be made from other hard materials, such as ceramic materials, including ceramic coated metals.

The cup component can be made from a polymeric material, especially when it is intended to provide the bearing surface within a metal cup which is fastened within a prepared cavity in the patient's bone. A polymeric bearing component can be fixed within a metal cup using existing techniques, for example using elastically deformable wires which fit into aligned grooves in the bearing component and cup.

Examples of applications for the cup component of the invention include as a component of a hip joint prostheses or a component of a shoulder joint prosthesis. The size of the component will depend on factors such as its intended application. For example, when the component is for use in a hip joint prosthesis, the radius of the generally spherical hollow region can be at least about 6 mm, sometimes at least about 8 mm, for example at least about 10 mm.

In larger products, the radius of the generally spherical hollow region can be at least about 15 mm, for example at least about 18 mm.

The radius of the generally spherical hollow region can be not more than about 40 mm, preferably not more than about 35 mm.

The thickness of the wall of the cup component will depend on factors such as its application, the material from which it is made, and the overall construction of the joint prosthesis. It will generally be preferred for the wall thickness (not including any coatings or other layers which are applied for fixation) to be as thin as possible to minimise the amount of bone which has to be resected from around the component, consistent with ensuring sufficient strength of the component, and ability to withstand wear due to articulation during use. When the component is made from a hard material such as a metal, a ceramic or a ceramic coated metal, and has a smooth internal bearing surface, its wall thickness will generally be at least about 1.5 mm, preferably at least about 2.0 mm, more preferably at least about 3.0 mm. When the component is made from a polymeric material (such as ultrahigh molecular weight polyethylene), its wall thickness might be at least about 2.5 mm, preferably at least about 3.0 mm, more preferably at least about 3.5 mm. The wall thickness of the component can vary between the polar and other regions. For example, the wall thickness can be greatest at the pole, and least at or close to the open mouth. For example, in the case of a component formed from a hard material, the wall thickness can be about 4 to 6 mm at the pole, and 3 to 4 mm at or close to the open mouth.

The characteristics of the internal surface for it to function satisfactorily as a bearing surface will depend on the material of the bearing surface and the overall construction of the joint prosthesis. When the component is made from a hard material such as a metal, a ceramic or a ceramic coated metal, the surface roughness of the internal bearing surface will preferably be not more than about 0.015 µm $R_a$, more preferably not more than about 0.01 μm $R_a$, especially not more than about 0.008 μm $R_a$, for example not more than about 0.005 μm $R_a$, as measured using conventional surface profilometer apparatus.

The component of the invention can be manipulated using an instrument which comprises a shaft, and a flange towards the end of the shaft on which the cup component can be fixed, which extends from the shaft transversely, and which can be retracted from an in-use position in which the flange can be received in a groove in the internal surface of the cup component, when positioned over the said end of the instrument, and a retracted position in which the flange is withdrawn towards the axis of the shaft from the position in which it can be received in a groove in the cup component, allowing the cup component to be released from the instrument.

The invention will now be described by way of example with reference to the accompanying drawings, in which.

Figure 1:
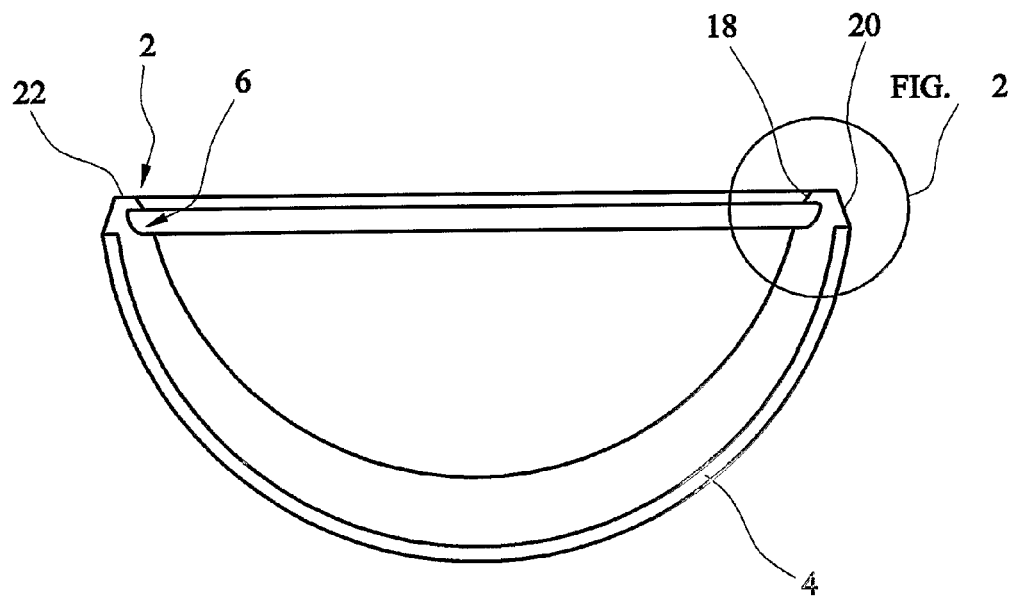
FIG. 1 is a cross-section through a cup component according to the invention.

Referring to the drawings, FIG. 1 shows an acetabular cup 2 which has a generally hemispherical shape. It is formed from a cobalt-chromium based alloy. The external surface of the cup has a porous layer 4 formed on it, which is provided by particles which are sintered so that they bond to one another and to the surface. The use of this technique to create a porous surface is known, and is used in connection with products sold by DePuy Orthopaedics Inc under the trade mark POROCOAT. Such a porous surface promotes fixation of the implant as a result of ingrowth of bone tissue.

A groove 6 is formed in the internal surface of the cup close to the open mouth 8. The groove is defined by an inner lip 10, an outer lip 12, and by opposite walls 14, 16 which are parallel at the open edge of the groove. Preferably, the walls of the groove are approximately perpendicular to the axis of polar the cup component.

The internal surface of the cup within the region defined by the inner lip 10 of the groove 6 is smooth and highly polished, so that it is substantially free of imperfections and its surface roughness is not more than about 0.015 μm $R_a$, preferably not more than about 0.01 μm $R_a$. Techniques for finishing the surface are known in connection with the manufacture of orthopaedic joint prosthesis components. The smooth polished region of the internal surface of the cup provides a bearing surface against which a correspondingly smooth convex bearing surface of another component can articulate. The radius of the bearing region will be selected according to the size of the bearing surface of the other component, and will generally be slightly bigger than that of the bearing surface of the other component.

The radius of the bearing region within the cup should preferably extend to the inner edge 10 of the groove 6 to provide for the largest range of articulation of the joint.

Figures 2, 4:
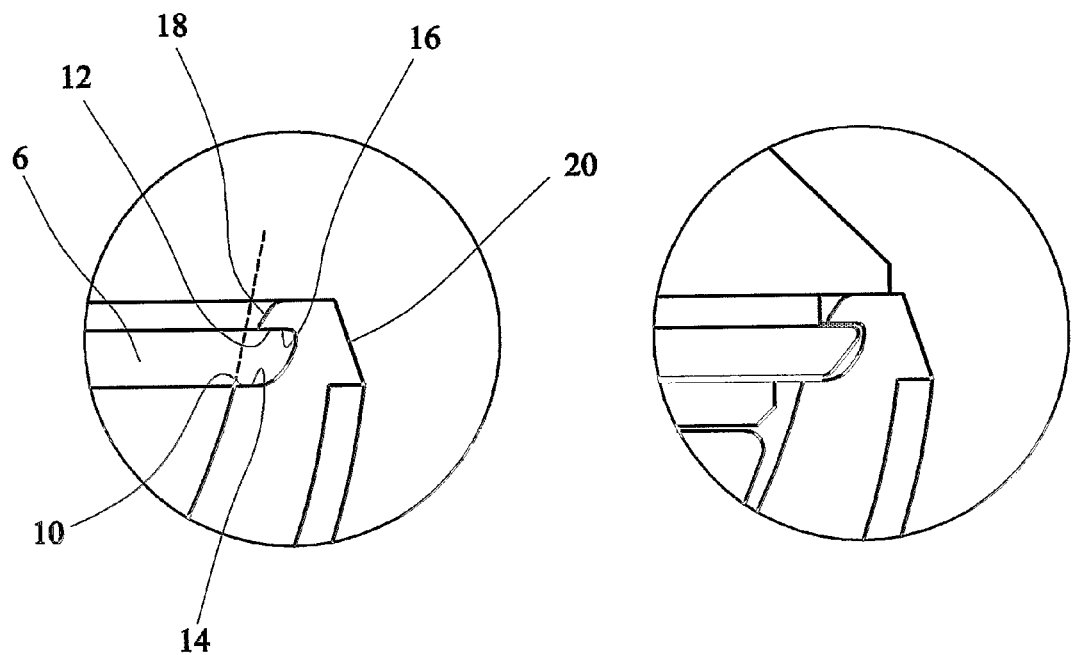
FIG. 2 is an enlarged view of the edge of the cup component shown in FIG. 1.
FIG. 4 is a view of the edge of the cup component as shown in FIG. 2, with the cup component attached to the instrument at one end thereof.

The radius of the hollow region within the cup at the outer lip 12 of the groove 6 is greater than the radius at the inner lip (measured from the centre of the sphere defined by the bearing surface). This can be seen in FIG. 2 by means of the dotted line continuation of the spherical surface beyond the inner lip. The ratio of the radius at the inner lip to the radius at the outer lip is less than about 0.98. The difference between the radii is about 1.0 mm.

The internal surface of the cup component is chamfered 18 between the outer lip 12 of the groove and the face of the component. The chamfered inner surface 18 helps to minimise restrictions on the range of articulation of the joint of the invention.

The external surface of the cup component is chamfered 20 close to the open mouth. The chamfer is provided over that part of the component which is intended to protrude from the cavity in the patient's bone in which the component is to be implanted. The angle between the chamfered surface and the tangent to the external spherical surface is at least about 30°, for example at least about 40°.

A planar face 22 is provided between the internal and external chamfered surfaces 18, 20. The groove is defined by parallel side walls 14, 16. The groove is rounded at the base of one of the walls.

Figure 3:
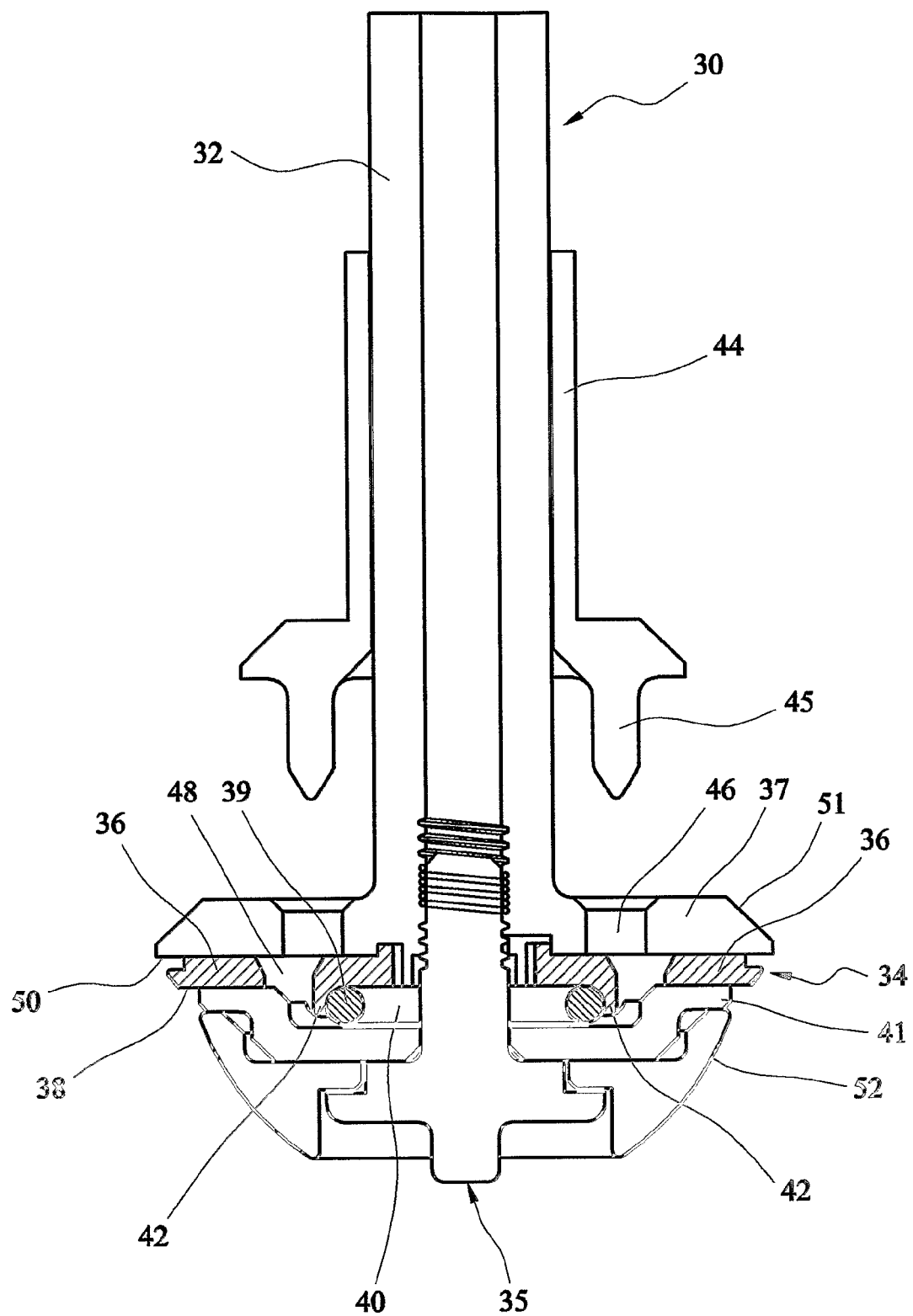
FIG. 3 is a cross-section through an instrument which can be used to manipulate the cup component shown in FIG. 1.

FIG. 3 shows an insertion instrument 30 which has a shaft 32. The shaft can extend to a handle (not shown) by which the instrument can be held and manipulated. The instrument includes a flange 34 towards one end 35. The flange extends transversely from the shaft.

The flange is made up of a plurality of flange portions 36, preferably four flange portions, which are spaced apart equally around the shaft. The flange portions can slide transversely relative to the axis which is defined by the shaft, between an in-use position in which the flange can be received in the groove 6 in the internal surface of the cup component, when positioned over the said end of the instrument, and a retracted position in which the flange is withdrawn towards the axis of the shaft from the position in which it can be received in the groove 6. The flange portions slide within a housing defined by a base plate 37 which, in the illustrated embodiment, is formed integrally with the housing. The housing also includes an opposing plate 41, opposite the base plate, so that the base plate and the opposing plate support the flange portions as they slide in the housing between in-use and retracted positions. The flange portions slide in the housing in a direction which is generally parallel to the flange. The opposing plate 41 supports the flange portions against forces directed along the shaft away from the end 35 of the shaft, which tend to separate the prosthesis component from the instrument.

The face 38 of each of the flange portions which faces towards the end of the shaft is chamfered.

The instrument includes a elastically compressible O-ring 39 which surrounds the shaft. The O-ring is retained within a slot 40 which extends transversely from the shaft.

The flange portions 36 are biassed towards their in-use positions by means of the O-ring 39 which acts against an upstand 42 on the flange portions.

The instrument includes a sliding collar 44 which bears a plurality of pins 45 extending from the collar in a direction parallel to the shaft axis, towards the end of the shaft. The pins are tapered at their ends.

Holes 46 are provided in the base plate 37 which are aligned with the pins 45 on the sliding collar. Holes 48 are also provided in each of the flange portions which, when the flange portions are in their retracted position, are aligned with the holes in the base plate and the pins on the sliding collar. However, when the flange portions are in their in-use positions, the holes 48 in the flange portions are displaced outwardly relative to the holes 46 in the base plate. The flange portions can then be displaced inwardly, against the force exerted on them by the O-ring 39 by moving the collar along the shaft, towards the end of the shaft, so that the pins 45 pass through the holes 48 in the base plate and the into the holes 46 in the flange portions. The displacement of the holes in the flange portions relative to the holes in the base plate is such that the tapered ends of the pins can be forced into the holes in the flange portions. This is facilitated by the holes in the flange portions being tapered at the ends which face towards the pins. Continued sliding of the collar along the shaft increases the inward displacement of the flange portions towards their retracted positions.

The face 50 of the base plate which faces towards the end of the instrument is planar. The edge 51 of the base plate is chamfered.

The instrument includes a cap 52 which surrounds the shaft, formed from a soft material such as a rubber or a polymer, which will not scratch the internal surface of the cup when it contacts that surface.

In use, a cup component 2 is fastened to an instrument 30 by forcing the instrument into the cup component. The action of the chamfered face 38 of the flange portions against the chamfered internal surface of the cup causes the flange portions to be displaced inwardly against the outward force exerted by the O-ring. The flange portions can then spring back towards the in-use position, as they are received in the groove 6. The cup component can then be manipulated using the instrument. Manipulation can include locating the cup component in a prepared recess within the patient's bone, aligning the cup component accurately, and also applying force along the axis of the shaft (which is aligned with the polar axis of the cup component) to force the cup into the recess. Force is applied to the cup through contact between the face 50 of the base plate 37 on the instrument and the planar face 22 on the cup between the chamfered internal and external surfaces 18, 20 (see FIG. 4). The chamfered edge 51 of the base plate, and the chamfered external surface 20 allows the surgeon to see the edge of the cup at the point (where the chamfered surface 20 and the porous coating 4 meet) which is intended to lie at the surface of the prepared cavity. This is important for the surgeon to be able to ensure that the cup has been implanted correctly.

Once the cup has been located and aligned accurately, the sliding collar 44 is moved along the shaft towards the end thereof, so that the pins 45 pass through the holes 48 in the base plate and the into the holes 46 in the flange portions. This causes the flange portions to be displaced inwardly towards the shaft so that they are no longer held within the groove in the cup component. This allows the instrument to be disengaged from the cup component.

The invention claimed is:

1. An instrument for positioning a cup component of an orthopedic joint prosthesis, the cup component having a mouth and an inner surface with a circumferential groove, the instrument comprising:
   an elongate shaft defining an axis, and having a distal end;
   a housing attached to the distal end of the shaft, the housing extending from the shaft transversely relative to the shaft axis, the housing comprising a base plate;
   at least two flange portions carried on the shaft, each of the at least two flange portions being configured to move relative to the base plate in a direction transverse to the shaft axis between an in-use position, where at least a portion of each of the at least two flange portions is received in the groove of the cup component, and a retracted position where the at least a portion of each of the at least two flange portions is moved towards the shaft axis so as to allow the cup component to be released from the instrument; and
   a unitary spring element disposed about the shaft axis and disposed between the at least two flange portions and the axis of the shaft, the spring element biasing each of the at least two flange portions towards the in-use position.

2. The instrument of claim 1, wherein the housing further comprises an opposing plate, and the flange portion is slidably disposed between the base plate and the opposing plate.

3. The instrument of claim 1, wherein the base plate is planar and has a plate surface and each of the at least two flange portions is planar and has a flange surface, and the plate surface of the base plate and flange surface of the flange portions are configured to slide relative to one another in the direction transverse to the shaft axis.

4. The instrument of claim 1, wherein the spring element is formed from a non-metallic material.

5. The instrument of claim 1, wherein the spring element is compressed elastically by each of the at least two flange portions when the flange portions are moved from the in-use position towards the retracted position.

6. The instrument of claim 5, wherein the spring element comprises an O-ring.

7. The instrument of claim 1, wherein each of the at least two flange portions is formed from a non-deformable material.

8. The instrument of claim 1, wherein each of the at least two flange portions is formed from a metal.

9. The instrument of claim 1, wherein the base plate has a surface configured to engage the mouth of the cup component to apply force to the cup component when the flange portions are in the in-use position.

10. The instrument of claim 1, wherein each of the at least two flange portions comprise a chamfered edge that is configured to contact the inner surface of the cup component when the flange portions are in the in-use position.

11. The instrument of claim 1, wherein the at least two flange portions comprise at least three radially spaced apart flange portions.

12. The instrument of claim 1, further comprising a soft cap at least partially disposed about the shaft and positioned between the at least two flange portions and the distal end of the shaft.

13. An assembly, comprising an instrument as claimed in claim 1, and a cup component of a joint prosthesis.

14. The instrument of claim 1, wherein the base plate has at least two base plate holes and each of the at least two flange portions has at least one flange hole, and further comprising a collar having at least two pins extending distally from the collar, the collar slidably connected to the shaft so as to slide between a first position, where the at least two flange portions are in the in-use position, and a second position, where one of the at least two pins are at least partially disposed within one of the at least two base plate holes and one of the at least two flange holes.

15. The instrument of claim 14, wherein each of the at least two flange portions has an upstand configured to contact the spring element, the upstand being displaced towards the shaft axis when the collar is in the second position to thereby move the at least two flange portions from the in-use position to the retracted position.

16. The instrument of claim 15, wherein, when the collar is in the second position, the upstands of the at least two flange portions compress the spring element.

17. The instrument of claim 14, wherein the at least two flange portions and the base plate are configured such that, when the collar is in the first position, the at least two base plate holes and the at least two flange holes are not aligned.

18. The instrument of claim 1, wherein the at least two flange portions are spaced apart radially with respect to one another relative to the shaft axis.

* * * * *